United States Patent
Montalbano et al.

(10) Patent No.: US 11,725,153 B2
(45) Date of Patent: Aug. 15, 2023

(54) PROCESS AND APPARATUS FOR RECOVERING CATALYST FROM A PRODUCT STREAM

(71) Applicant: UOP LLC, Des Plaines, IL (US)

(72) Inventors: Joseph A. Montalbano, Elmhurst, IL (US); John J. Senetar, Naperville, IL (US); Nasim Ghazinoor, Hoffman Estates, IL (US); Richard A. Johnson, II, Algonquin, IL (US); Lev Davydov, Northbrook, IL (US)

(73) Assignee: UOP LLC, Des Plaines, IL (US)

( * ) Notice: Subject to any disclaimer, the term of this patent is extended or adjusted under 35 U.S.C. 154(b) by 52 days.

(21) Appl. No.: 17/230,871

(22) Filed: Apr. 14, 2021

(65) Prior Publication Data

US 2021/0324278 A1 Oct. 21, 2021
US 2022/0315845 A9 Oct. 6, 2022

Related U.S. Application Data

(60) Provisional application No. 63/011,634, filed on Apr. 17, 2020.

(51) Int. Cl.
*C10G 55/06* (2006.01)
*B01D 53/14* (2006.01)
(Continued)

(52) U.S. Cl.
CPC ......... *C10G 55/06* (2013.01); *B01D 53/1418* (2013.01); *B01D 53/1425* (2013.01);
(Continued)

(58) Field of Classification Search
CPC ........ C10G 11/18; C10G 55/06; B01D 47/06; B01D 47/14; B01D 53/1418;
(Continued)

(56) References Cited

U.S. PATENT DOCUMENTS 2,384,378 A * 9/1945 Hooker ............... C07C 7/12
95/181
5,354,431 A * 10/1994 Taylor ............... C07D 301/32
203/64
(Continued)

FOREIGN PATENT DOCUMENTS

WO 2017079004 A1 5/2017

OTHER PUBLICATIONS

"PCT Search Report and Written Opinion", dated Aug. 5, 2021.

*Primary Examiner* — Brian A McCaig
(74) *Attorney, Agent, or Firm* — Paschall & Associates, LLC; James C. Paschall (57) ABSTRACT

A process for recovering catalyst from a fluidized catalytic reactor effluent is disclosed comprising reacting a reactant stream by contact with a stream of fluidized catalyst to provide a vaporous reactor effluent stream comprising catalyst and products. The vaporous reactor effluent stream is contacted with a liquid coolant stream to cool it and transfer the catalyst into the liquid coolant stream. A catalyst lean vaporous reactor effluent stream is separated from a catalyst rich liquid coolant stream. A return catalyst stream is separated from the catalyst rich liquid coolant stream to provide a catalyst lean liquid coolant stream, and the return catalyst stream is transported back to said reacting step.

20 Claims, 1 Drawing Sheet

(51) Int. Cl.
  *B01D 53/18* (2006.01)
  *B01J 8/00* (2006.01)
  *B01J 8/18* (2006.01)
  *B01J 8/24* (2006.01)
  *B60K 17/02* (2006.01)
  *B60K 17/24* (2006.01)
  *B60K 17/348* (2006.01)
  *B60K 17/356* (2006.01)
  *B60K 23/08* (2006.01)
  *B60K 23/04* (2006.01)

(52) U.S. Cl.
  CPC ............ *B01D 53/185* (2013.01); *B01J 8/006* (2013.01); *B01J 8/1863* (2013.01); *B01J 8/24* (2013.01); *B60K 17/02* (2013.01); *B60K 17/24* (2013.01); *B60K 17/348* (2013.01); *B60K 17/356* (2013.01); *B60K 23/0808* (2013.01); *B01D 2252/00* (2013.01); *B01J 2208/00761* (2013.01); *B60K 2023/046* (2013.01); *B60K 2023/0816* (2013.01); *C10G 2300/706* (2013.01)

(58) Field of Classification Search
  CPC ............ B01D 53/1425; B01D 53/185; B01D 2247/04; B01D 2252/00; B01J 8/006; B01J 8/1863; B01J 8/24; B01J 8/26; B01J 2208/00761; B60K 17/02; B60K 17/24; B60K 17/3462; B60K 17/348; B60K 17/356; B60K 23/0808; B60K 2023/043; B60K 2023/046; B60K 2023/085; B60K 2023/0816; C07C 7/09; B60Y 2300/82; B60Y 2400/804
  See application file for complete search history.

(56) References Cited

U.S. PATENT DOCUMENTS

| | | |
|---|---|---|
| 6,165,368 A | 12/2000 | Zamarripa |
| 8,877,997 B2 | 11/2014 | Montalbano et al. |
| 2004/0069684 A1 | 4/2004 | Tallman et al. |
| 2009/0178954 A1* | 7/2009 | Kanyuh .................. C07C 4/02 208/100 |
| 2020/0197891 A1 | 6/2020 | Pretz |
| 2021/0077967 A1 | 3/2021 | Reyneke et al. |

* cited by examiner

PROCESS AND APPARATUS FOR RECOVERING CATALYST FROM A PRODUCT STREAM

CROSS-REFERENCE TO RELATED APPLICATIONS

This application claims priority from provisional application 63/011,634, filed Apr. 17, 2020, incorporated herein in its entirety.

FIELD

The field is the recovery of catalyst from a reactor effluent stream and particularly from a fluidized catalytic reactor effluent stream.

BACKGROUND

Fluidized catalytic reactions are conducted at elevated temperatures with fluidized catalyst that is free to move out of the reactor. Hot vaporous effluent exiting the fluidized catalytic reactor carries a loading of catalyst fines despite equipment designed to retain catalyst in the reactor or remove it from reactor effluent. Downstream equipment is necessary to cool the reactor effluent and to remove catalyst therefrom. Fluidized catalytic processes include fluid catalytic cracking (FCC), methanol-to-olefins OTTO), toluene methylation (TM) and paraffin dehydrogenation (PDH). Reactor effluent that contains catalyst can foul downstream equipment if not captured.

In applications, light olefin production is vital to the production of sufficient plastics to meet worldwide demand. PDH is a process in which light paraffins such as ethane and propane can be dehydrogenated to make ethylene and propylene, respectively. Dehydrogenation is an endothermic reaction which requires external heat to drive the reaction to completion. In PDH, heavy hydrocarbon byproducts are produced that must be separated from the light olefin products.

Fluid catalytic cracking (FCC) is another endothermic process which produces ethylene and propylene.

In PDH and FCC reactions with fluidized catalyst, coke can deposit on the catalyst while catalyzing the reaction. The catalyst may be regenerated in a catalyst regenerator by combusting coke from the catalyst in the presence of oxygen. The hot regenerated catalyst may then be transferred back to the reactor to catalyze the reaction.

There is a need for improved methods of recovering catalyst from reactor effluent. Fluidized catalytic systems rely on effective capture of the catalyst to maintain the catalyst within the system. This method of catalyst capture varies depending on the application. One common means of capture is the use of one or more disengaging steps in series that utilize impingement, flow redirection, and/or cyclonic separation. Cyclones are widely used in the industry and are particularly useful for separation of catalyst from the fluidizing medium.

Cyclones may exhibit high efficiency, such as greater than 99.99% for particles larger than 20 microns. However, the efficiency of particle capture rapidly decreases as size of the solids decrease below 20 microns. Increased cyclone capture efficiency may be attained at the sacrifice of additional pressure drop. The velocity required for cyclonic separation is high, often exceeding 20 m/s. High velocity leads to additional attrition of the entrained solids and thereby creation of additional fines, mostly less than 20μ in diameter, which are not captured in the cyclones.

Filters can be extremely effective for trapping entrained particles. Filters may be placed directly in fluidized catalyst effluent lines as an alternative to cyclones, or as secondary capture downstream of cyclones. Although effective, filters are expensive and may be cost prohibitive. Filters also introduce additional pressure drop, fouling and plugging concerns. Filters are more amenable to regenerator flue gas where the absence of heavy hydrocarbon byproduct does not present a great risk of fouling.

There is a need for improved processes for recovering catalyst particles from reactor effluent streams.

BRIEF SUMMARY

A process for recovering catalyst from a fluidized catalytic reactor effluent stream is disclosed comprising reacting a reactant stream by contact with a stream of fluidized catalyst to provide a vaporous reactor effluent stream comprising catalyst and products. The vaporous reactor effluent stream is contacted with a liquid coolant stream to cool it, scrub catalyst particles, and transfer the catalyst into the liquid coolant stream. A catalyst lean vaporous reactor effluent stream is separated from a catalyst rich liquid coolant stream. A return catalyst stream is separated from the catalyst rich liquid coolant stream to provide a catalyst lean liquid coolant stream, and the return catalyst stream is transported back to said reacting step. The coolant may be a solvent that absorbs the heavy hydrocarbon byproducts from the effluent stream.

The process described herein is an alternative to using a filter for direct solids recovery from fluidized catalytic reactor effluent. The benefit of the process is a high efficiency method for catalyst recovery from the process. The process may also provide a simultaneous removal of heavy hydrocarbon byproducts which can promote equipment fouling and plugging.

In addition, the described catalyst recovery process combined with fluidized catalytic dehydrogenation process requirements provides a surprising synergy for fines recycle within the process.

Definitions

Figure 1:
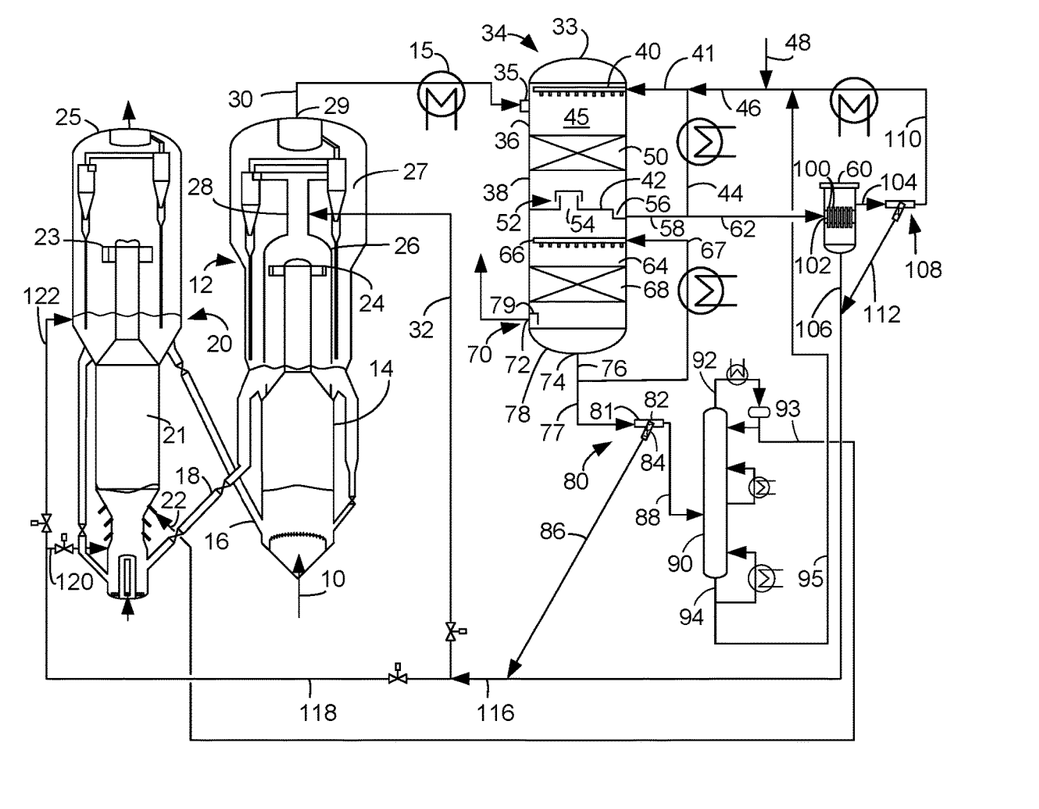
The FIG. is a schematic drawing of a process of the present disclosure.

The term "communication" means that fluid flow is operatively permitted between enumerated components, which may be characterized as "fluid communication".

The term "downstream communication" means that at least a portion of fluid flowing to the subject in downstream communication may operatively flow from the object with which it fluidly communicates.

The term "upstream communication" means that at least a portion of the fluid flowing from the subject in upstream communication may operatively flow to the object with which it fluidly communicates.

The term "direct communication" means that fluid flow from the upstream component enters the downstream component without passing through any other intervening vessel.

The term "indirect communication" means that fluid flow from the upstream component enters the downstream component after passing through an intervening vessel.

The term "bypass" means that the object is out of downstream communication with a bypassing subject at least to the extent of bypassing.

The term "fuel gas" comprises hydrocarbons, hydrogen and mixtures thereof.

As used herein, the term "predominant" or "predominate" means greater than 50%, suitably greater than 75% and preferably greater than 90%.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottoms stream back to the bottom of the column. Feeds to the columns may be preheated. The top pressure is the pressure of the overhead vapor at the vapor outlet of the column. The bottom temperature is the liquid bottom outlet temperature. Overhead lines and bottoms lines refer to the net lines from the column downstream of any reflux or reboil to the column. Stripper columns may omit a reboiler at a bottom of the column and instead provide heating requirements and separation impetus from a fluidized inert media such as steam.

Stripping columns typically feed a top tray and take main product from the bottom.

As used herein, the term "separator" means a vessel which has an inlet and at least an overhead vapor outlet and a bottoms liquid outlet and may also have an aqueous stream outlet from a boot. A flash drum is a type of separator which may be in downstream communication with a separator that may be operated at higher pressure.

The term "Cx" is to be understood to refer to molecules having the number of carbon atoms represented by the letter "x". Similarly, the term "Cx−" refers to molecules that contain less than or equal to x and preferably x and less carbon atoms. The term "Cx+" refers to molecules with more than or equal to x and preferably x and more carbon atoms.

As used herein, the term "a component-rich stream" means that the rich stream coming out of a vessel has a greater concentration of the component than the feed to the vessel.

As used herein, the term "a component-lean stream" means that the lean stream coming out of a vessel has a smaller concentration of the component than the feed to the vessel.

DETAILED DESCRIPTION

The disclosure provides a process that cools hot vaporous reactor effluent and recovers catalyst therefrom for return to the process and apparatus. The teachings herein may be applicable to any process and apparatus that utilizes catalyst that is fluidized in a reactor. PDH, MTO, TM and FCC are examples of such processes. For example, FCC catalyst is used to crack larger hydrocarbon molecules to smaller hydrocarbon molecules at around atmospheric pressure and about 427° C. (800° F.) to 538° C. (1000° F.) and a catalyst to oil ratio of about 5 to about 30. MTO catalyst is used to convert oxygenates such as methanol or dimethyl ether to olefins at about 200 to 575° C. and a pressure of about 65 to about 500 kPa (gauge). PDH catalyst is used in a dehydrogenation reaction process to catalyze the dehydrogenation of ethane and/or propane to ethylene and propylene. The PDH process will be described exemplarily to illustrate the disclosed apparatus and process. The described process also has synergy with the PDH process by enabling removal of heavy hydrocarbon byproducts simultaneously with catalyst removal.

An exemplary PDH process is shown in the FIGURE. A reactant stream in line 10 concentrated in propane may be prepared by depropanizing a liquefied petroleum gas stream to separate a reactant stream concentrated in propane and ethane from heavier hydrocarbons. The reactant stream is preheated in heat exchangers including a feed-effluent heat exchanger and fed to a reactor 12. In the reactor 12, the reactant stream may be fed to a riser 14 and reacted by contact with a stream of fluidized regenerated catalyst from a conduit 16. The reactant stream and the stream of fluidized catalyst both travel up the riser 14 while catalytically converting reactants to products. An initial separation of product gases from catalyst may be performed by an initial separator 24 with tangential arms that sling catalyst and product gas tangentially in a cylindrical containment vessel 26. The swirling angular movement of the product gases and catalyst effect a separation of catalyst from product gas by centripetal acceleration. The separated catalyst loses momentum and falls downwardly into a bed of catalyst while separated product gases rise in the reactor 12. The initial separator may also be a ballistic-style separator. A gas recovery conduit 28 carries product gases upwardly to further separation from entrained catalyst in equipment such as cyclones 27. A vaporous reactor effluent stream comprising a light loading of residual catalyst and all gaseous products is discharged from the reactor 12 through a reactor outlet 29 in line 30. Hot product gases may be quenched in the reactor 12 downstream of the initial separation of catalyst in the initial separator 24 such as in the gas recovery conduit 28 located between the initial separator 24 and the reactor outlet 29. Quenching may occur between the initial separator 24 and the cyclones 27. The quench medium may be delivered by line 32 to the reactor 12 such as to the gas recovery conduit 28.

The conditions in the dehydrogenation reaction may include a temperature of about 500 to about 800° C., a pressure of about 40 to about 310 kPa and a catalyst-to-oil ratio of about 5 to about 100. The dehydrogenation reaction may be conducted in a fluidized manner such that gas, which may be the reactant paraffins or a fluidizing inert gas, is distributed to the reactor in a way that lifts the dehydrogenation catalyst in the reactor vessel while catalyzing the dehydrogenation of propane, ethane and/or other hydrocarbons. During the catalytic dehydrogenation reaction, coke is deposited on the dehydrogenation catalyst so as to reduce the activity of the catalyst. The dehydrogenation catalyst must then be regenerated.

The spent dehydrogenation catalyst is transported by a conduit 18 to a regenerator 20 to combust the coke and regenerate the spent catalyst into regenerated catalyst. The catalyst regenerator 20 includes a combustion chamber 21 and a catalyst separator 23 which separates regenerated catalyst from flue gas generated in the combustion chamber 20 as it enters a separation chamber 25. An oxygen supply gas is provided to the combustion chamber 21 which lifts the spent catalyst in the combustion chamber 21 into the separation chamber 25. The coke is burned off the spent catalyst by contact with the oxygen supply gas at regeneration conditions. In an exemplary embodiment, air is used as the oxygen supply gas, because air is readily available and provides sufficient oxygen for combustion. About 10 to about 15 kg of air are required per kg of coke burned off of the spent catalyst. Exemplary regeneration conditions include a temperature from about 500° C. (900° F.) to about 900° C. (1700° F.) and a pressure of about 103 kPa (abs) (15 psia) to about 450 kPa (abs) (70 psia) in the regenerator 20.

Regenerated catalyst is returned to the reactor 12 in the conduit 16. Hydrocarbon fuel may be added to the regenerator such as by line 22 to boost the heat generated therein.

The dehydrogenation catalyst may be of any of a variety of catalysts suitable for a fluidized dehydrogenation unit. The dehydrogenation catalyst selected should minimize cracking reactions and favor dehydrogenation reactions. Suitable catalysts for use herein include amorphous material or molecular sieves which may be dispersed in a porous inorganic carrier material such as silica, aluminum, zirconium, or clay. An exemplary embodiment of a catalyst includes crystalline silica-alumina or silica-alumina-phosphate as the primary active component, a matrix, a binder, and a filler.

The primary active component ranges from about 10 to about 50 weight percent of the catalyst and may have a lattice structure that limits the size range of hydrocarbon molecules that can enter the lattice. The molecular sieves appropriate for the primary active component should have medium and smaller average pore size. Typically, molecular sieves with medium and smaller average pore size have pores with openings of no more than 0.7 nm in effective diameter defined by rings of ten or fewer.

The matrix component may include amorphous alumina or silica, and the binder and filler provide physical strength and integrity. Silica sol or alumina sol may be used as the binder and kaolin clay may be used as the filler. The catalyst particles may have a nominal diameter of about 20 to about 150 micrometers with the average diameter of about 70 to about 90 micrometers.

The dehydrogenation catalyst may support a dehydrogenation metal. The dehydrogenation metal may be a one or a combination of transition metals. A noble metal may be a preferred dehydrogenation metal; however, a IIB or a IIIB metal may be a suitable dehydrogenation metal alone or in combination with other dehydrogenation metals. Iron, tungsten, gallium, copper, zinc or zirconium alone or in combination with each other or a noble metal may be suitable dehydrogenation metals. Combustion promoters may be utilized in addition to the catalyst. Metals may be incorporated into the lattice structure of the molecular sieve.

The acid function of the catalyst should be minimized to prevent cracking and favor dehydrogenation. Alkali metals and alkaline earth metals may be also be included in the catalyst to attenuate the acidity of the catalyst. Rare earth metals may be included in the catalyst to control the activity of the catalyst. Concentrations of 0.05 to 10 wt % metals may be incorporated into the catalyst. In the case of the noble metals, it is preferred to use about 0.05 to about 2 wt % noble metal.

The vaporous reactor effluent stream in line 30 comprises light hydrocarbon and heavy hydrocarbon products and entrained catalyst. The catalyst is predominantly catalyst fines which have a largest diameter of no more than 40μ and preferably no more than 20μ. The vaporous reactor effluent stream may be cooled in cooler 15 such as an effluent cooler and fed to a contact cooler 34 through a cooler inlet nozzle 35. The contact cooler 34 may have a top 33 comprising a hemispherical head. The contact cooler 34 may also comprise a first chamber 36 that may be defined by the top 33 of the contact cooler 34, an outer wall 38 and a first vapor liquid separator 42. The cooler inlet nozzle 35 may comprise a nozzle that is located in the outer wall 38, but it may be located in the top 33 of the contact cooler. The cooler inlet nozzle 35 may be in downstream communication with the reactor 12 and feed the hot vaporous reactor effluent stream to the first chamber 36 and the contact cooler 34.

The contact cooler 34 comprises a co-current contacting of the vaporous reactor effluent stream and cooling liquid. Although co-current contacting is the preferred embodiment, one could utilize countercurrent contacting in one or more of various contacting sections. Countercurrent contacting increases the effectiveness of cooling and thus allows a closer temperature approach between the reactor effluent and the quenching medium. Co-current contacting is preferred for enhancing capture of catalyst fines. However, there may be other overriding concerns that may outweigh the benefit of co-current contacting in favor of countercurrent contacting.

A first coolant distributor 40 with an array of lower liquid spray nozzles is located directly above the reactor effluent inlet nozzle 35 or directly below the nozzle if the nozzle is in the top. The lower liquid spray nozzles feed and spray a first liquid coolant stream from a line 41 downwardly onto the hot vaporous reactor effluent stream to cool the hot vaporous reactor effluent stream. The first liquid coolant stream contacts the vaporous reactor effluent stream to cool the vaporous reactor effluent stream to near its dew point while leaving it in the vapor phase. Moreover, the contacting also transfers catalyst from the vaporous reactor effluent stream into the first liquid coolant stream to provide a catalyst rich liquid coolant stream. Additionally, the first liquid coolant stream may be a solvent that absorbs heavier hydrocarbons such as C4+ hydrocarbons into the solvent liquid phase, while leaving C3− hydrocarbons in the vapor phase.

The first liquid coolant stream in line 41 may comprise a first cooled pump-around coolant stream in line 44, a first recycled coolant stream in line 46 and a make-up coolant stream in line 48 which combine to provide the first liquid coolant stream in line 41. The first liquid coolant stream may have a temperature in the range of about 30° C. to about 65° C. The spray nozzles typically have a conical spray pattern and an advantageous droplet size distribution to maximize capturing particulates in the liquid phase. Spray nozzles may be pointed downwardly, but additional spray nozzles on the first coolant distributor 40 may be pointed upwardly at the top of the contact cooler 34 to prevent fine catalyst particle accumulation on the top of the vessel.

The liquid coolant stream should be capable of selectively absorbing the heavy hydrocarbon products in the reactor effluent stream while leaving the light hydrocarbon products in the reactor effluent stream. The coolant may be a C9+ hydrocarbon stream that will be readily separable from the heavy hydrocarbon products in the reactor effluent stream. A suitable coolant stream may comprise a stream comprising C9-C11 hydrocarbons such as a bottoms stream from a heavy aromatics column from an aromatics complex. Suitably, at least 50 wt % and preferably at least 70% of the coolant stream comprises hydrocarbons with at least nine carbon atoms.

The quantity of the coolant stream pumped to the first coolant distributor 40 will be 100-110% of the coolant necessary to bring the temperature in the first chamber 36 to a temperature of about 60° C. to about 90° C. The spray nozzles will be located with sufficient clearance from interior surfaces in the contact cooler 34 to enable full development of the intended spray pattern. The typical clearance is about 0.3 to about 3 meters. The space located directly below the reactor effluent inlet nozzle 35 in which the coolant stream will contact the hot vaporous reactor effluent stream may be termed a desuperheating zone 45 because the vaporous hot reactor effluent stream is desuperheatead but remains in the vapor phase.

In the first chamber 36 the liquid coolant stream also captures catalyst particles to transfer them into the liquid phase. A first bed 50 may be located below the desuperheating zone 45 and the reactor effluent inlet nozzle 35 to facilitate particle capture. Liquid droplets from the first coolant distributor 40 are sized to capture catalyst particles as well as wetting the first bed 50 to enable capture of particulates into the liquid phase. An additional coolant liquid distributor may be utilized to further wet the first bed 50 for particle capture.

The first bed 50 may comprise a structured packing which may comprise a grid of adjoining metal corrugated plates stacked in layers to foster circuitous travel through the bed to promote contacting between the liquid and the vapor. The packing in the first bed 50 should be fouling-resistant for severe service. Suitable packing should have minimal horizontal surfaces to minimize catalyst hold up such as with a surface area per unit volume of less than about 90 $m^2/m^3$, suitably less than about 70 $m^2/m^3$ and preferably less than about 40 $m^2/m^3$. Suitable structured packing may have a free volume of at least 95%. Random packing may also be used in the bed 40, but it should be fouling resistant. Typical examples of structured packing that may be used are Proflux by Koch Glitsch, Raschig Grid Packing and Mellagrid by Sulzer.

The liquid coolant sprayed onto the first bed 50 wets the packing. The coolant liquid will sufficiently wet the packing in the first bed 50 to prevent particle accumulation and fouling in the bed. Adequate wetting of the packing will also maximize catalyst wetting and capture into the liquid phase throughout the first bed 50. The coolant stream distributor 40 and the reactor effluent inlet nozzle 35 should preferably be disposed on the same vertical side of the first bed 50 and preferably above the bed, in an embodiment, to provide downward, co-current flow through the bed. However, counter-current flow is also envisioned.

The coolant stream and the vaporous reactor effluent stream pass together through the first bed 50 in a co-current flow arrangement while disengaging catalyst from the vaporous reactor effluent stream to reduce its catalyst loading and transferring the catalyst into the coolant stream to increase its catalyst loading. Particle transfer from the vaporous reactor effluent stream into the liquid coolant stream and additional heat exchange will occur in the first bed 50. The bed will also promote mixing to increase absorption of the heavy hydrocarbon products by the coolant stream to increase its heavy hydrocarbon product concentration.

The liquid coolant stream with an increased loading of catalyst comprising a first catalyst rich, heavy hydrocarbon rich coolant stream is separated in the first vapor liquid separator 42 below the first bed 50 from the vaporous reactor effluent stream with a decreased loading of catalyst and a decreased concentration of heavy hydrocarbon products comprising a catalyst lean, heavy hydrocarbon lean vaporous reactor effluent stream at the bottom of the first chamber 36. The first vapor liquid separator 42 may be a chimney tray. The first vapor liquid separator 42 may have one or more chimneys 52 each comprising an open vertical tube extending upwardly from and sealed to the tray and aligned with a respective opening or vapor passage 54 in the tray with a cap over a respective open tube. The tube in the chimney 52 allows a liquid level to develop on the tray which is designed to rise to below the top of the open tube. The cap on the tube of the chimney 52 prevents descending liquid from passing through the chimney and through vapor passage 54 in the tray. Normally, only the catalyst lean, heavy hydrocarbon lean vaporous reactor effluent stream passes in a circuitous route through the chimney 52 from the first chamber 36 through vapor passage 54 to the other vertical side of, such as below, the first vapor liquid separator 42 to an exit or a downstream chamber.

A well 56 at a periphery of the tray of the first vapor liquid separator 42 collects the catalyst rich, heavy hydrocarbon rich liquid coolant stream separated from the vapor. The first catalyst rich liquid, heavy hydrocarbon rich coolant stream collected in the well is discharged from a liquid outlet from the first chamber 36 into line 58. A portion of the first catalyst rich, heavy hydrocarbon rich liquid coolant stream is recycled as the first cooled pump-around coolant stream in line 44 through a cooler and fed back to the first coolant distributor 40. The remainder of the first catalyst rich, heavy hydrocarbon rich liquid coolant stream is fed to a catalyst separation vessel 60 in line 62. The loading of catalyst and concentration of heavy hydrocarbons in the first coolant stream fed to the first chamber 36 in the liquid coolant stream is determined by the proportions of coolant added from lines 44 and 46 to make the liquid coolant stream fed to the first coolant distributor 40 in line 41. The catalyst rich coolant stream is taken from the contact cooler 34 at an intermediate location in the contact cooler.

The vapor liquid separator 52 may require agitation or flushing to prevent accumulation of catalyst and disruption of operation. Extra nozzles and liquid inlet devices may be provided in the vicinity of the vapor liquid separator 52 to reduce the risk of particulate buildup in stagnant zones of the tray which may otherwise agglomerate catalyst. The chimney tray may be sloped or slanted toward the well 56 to facilitate particle collection to reduce the risk of disruption of operation.

The contact cooler 34 may include a second chamber 64. The catalyst lean, heavy hydrocarbon lean reactor effluent stream enters the second chamber 64 through the vapor passage 54.

A second coolant stream distributor 66 with an array of liquid spray nozzles is located below the vapor passage 54. The lower liquid spray nozzles feed and spray a second liquid coolant stream from a line 67 downwardly onto the catalyst lean, heavy hydrocarbon lean reactor effluent stream to cool the catalyst lean, heavy hydrocarbon lean reactor effluent stream. The second liquid coolant stream contacts the vaporous catalyst lean, heavy hydrocarbon lean reactor effluent stream to cool the catalyst lean, heavy hydrocarbon lean reactor effluent stream to its dew point while leaving it in the vapor phase. Moreover, the contacting also transfers remaining catalyst from the catalyst lean, heavy hydrocarbon lean reactor effluent stream into the second liquid coolant stream to provide a second catalyst rich liquid coolant stream. Additionally, the second liquid coolant stream may be a solvent that absorbs heavier hydrocarbons such as C4+ hydrocarbons into the solvent liquid phase to provide a second heavy hydrocarbon rich liquid coolant stream, while leaving C3− hydrocarbons in the vapor phase.

The second liquid coolant stream in line 67 may comprise a second cooled pump-around coolant stream taken from a liquid outlet 74 of the second chamber 64. The second liquid coolant stream may have a temperature in the range of about 30° C. to about 70° C. or preferably about 40° C. to about 65° C. The spray nozzles typically have a conical spray pattern and an advantageous droplet size distribution to maximize capturing particulates in the liquid phase. Spray nozzles may be pointed downwardly, but additional spray nozzles on the second coolant distributor 66 may be pointed upwardly at the top of the contact cooler 34 to prevent fine catalyst particle accumulation on the top of the vessel.

The liquid coolant stream should be capable of selectively absorbing the heavy hydrocarbon products in the catalyst lean, heavy hydrocarbon lean reactor effluent stream while leaving the light hydrocarbon products in the reactor effluent stream. The coolant may be a C9+ hydrocarbon stream that will be readily separable from the heavy hydrocarbon products in the reactor effluent stream. A suitable coolant stream may comprise a stream comprising C9-C11 hydrocarbons such as a bottoms stream from a heavy aromatics column from an aromatics complex. Suitably, at least 50 wt % and preferably at least 70% of the coolant stream comprises hydrocarbons with at least nine carbon atoms. The second coolant stream may have the same underlying composition as the first coolant stream and both may be ultimately supplied by the same make up line 48.

The quantity of the coolant stream pumped to the second coolant distributor 66 will be 100-110% of the coolant necessary to bring the temperature in the second chamber 64 to about 30° C. to about 70° C. The spray nozzles will be located with sufficient clearance from interior surfaces in the second chamber 64 to enable full development of the intended spray pattern. The typical clearance is about 0.3 to about 3 meters.

In the second chamber 64 the liquid coolant stream also captures additional catalyst particles to transfer them into the liquid phase. A second bed 68 may be located below the vapor inlet 54 and second coolant distributor 66 to facilitate particle capture. Liquid droplets from the second coolant distributor 66 are sized to capture catalyst particles as well as wetting the second bed 68 to enable capture of particulates into the liquid phase.

The second bed 68 may comprise a structured packing which may comprise a grid of adjoining metal corrugated plates stacked in layers to foster circuitous travel through the bed to promote contacting between the liquid and the vapor. The packing in the second bed 68 should be fouling-resistant for severe service. Suitable packing should have minimal horizontal surfaces to minimize catalyst hold up such as with a surface area per unit volume of less than about 90 m$^2$/m$^3$, suitably less than about 70 m$^2$/m$^3$ and preferably less than about 40 m$^2$/m$^3$. Suitable structured packing may have a free volume of at least 95%. Random packing may also be used in the second bed 68, but it should be fouling resistant. Typical examples of structured packing that may be used are Proflux by Koch Glitsch, Raschig Grid Packing and Mellagrid by Sulzer.

The second liquid coolant sprayed onto the second bed 68 wets the packing. The second coolant liquid will sufficiently wet the packing in the second bed 68 to prevent particle accumulation and fouling in the bed. Adequate wetting of the packing will also maximize catalyst wetting and capture into the liquid phase throughout the second bed 68. The second coolant distributor 66 and the vapor passage 54 should be disposed on the same side of the second bed 68 and preferably above the bed, in an embodiment, to provide downward flow through the bed.

The second coolant stream and the catalyst lean, heavy hydrocarbon lean reactor effluent stream pass together through the second bed 68 in a co-current flow arrangement while disengaging catalyst from the catalyst lean, heavy hydrocarbon lean reactor effluent stream to further reduce its catalyst loading and transferring the catalyst into the second coolant stream to increase its catalyst loading. Particle transfer from the catalyst lean, heavy hydrocarbon lean reactor effluent stream into the second liquid coolant stream and additional heat exchange will occur in the second bed 68. The second bed 68 will also promote mixing to increase absorption of the heavy hydrocarbon products by the second coolant stream to increase its heavy hydrocarbon product concentration.

The second liquid coolant stream obtains an increased loading of catalyst resultingly comprising a second catalyst rich, heavy hydrocarbon rich coolant stream. The catalyst lean, heavy hydrocarbon lean reactor effluent stream obtains a decreased loading of catalyst and a decreased concentration of heavy hydrocarbon products resulting in a further catalyst lean, further heavy hydrocarbon lean vaporous reactor effluent stream. At the bottom of the second chamber 64, the second catalyst rich, heavy hydrocarbon rich coolant stream is separated in a second vapor liquid separator 70 below the second bed 68 from the further catalyst lean, further heavy hydrocarbon lean vaporous reactor effluent stream. The second vapor liquid separator 70 may be structured as a second vapor passage 72 that is above a liquid outlet 74 and above a bottom 78 of the second chamber 64. The second catalyst rich, heavy hydrocarbon rich coolant stream is drawn off through the liquid outlet 74 into line 76. The liquid outlet 74 may be located in the bottom 78 of the second chamber 64. The further catalyst lean, further heavy hydrocarbon lean vaporous reactor effluent stream is removed through the second vapor passage 72 at an elevation above the liquid outlet 74 effecting a separation of the further catalyst lean, further heavy hydrocarbon lean vaporous reactor effluent stream from the second catalyst rich, heavy hydrocarbon rich coolant stream. The vapor passage 72 may be equipped with a baffle 79 above the vapor passage to ensure that descending material must reverse direction once below a lower edge of the baffle before passing through the vapor passage to prevent liquid from passing through the vapor passage. It is also envisioned that the liquid outlet 74 could be located in the side of the second chamber 74. In an illustrated embodiment, the second chamber 90 is defined by the first vapor liquid separator 42, the outer wall 38 and the bottom 78.

The contact cooler 34 may operate at a pressure of about 0 to about 50 kPa (gauge).

The second catalyst rich, heavy hydrocarbon rich coolant stream in line 76 is split between the second coolant stream in line 67 and a final catalyst rich, heavy hydrocarbon rich coolant stream in line 77. The second coolant stream in line 67 is cooled and pumped around to the second coolant distributor 66 to be distributed back to the second chamber 64. The final catalyst rich, heavy hydrocarbon rich coolant stream in line 77 must be fractionated to separate the absorbed heavy hydrocarbon products from the coolant. Prior to fractionation, the final catalyst rich, heavy hydrocarbon rich coolant stream may be fed to a first catalyst filter 80.

The first catalyst filter 80 may be a centrifuge, a hydrocyclone, a barrier filter or other means of separating solids from liquid. In an embodiment, the catalyst filter 80 is a strainer 81. A strainer 81 may comprise an in-line fluid passage 82 with a pipe basket 84 interposed in the passage at a supplementary angle to the passage. The basket 84 may have perforations that allow fluid to pass through the passage 82 but tend to capture the solids which exit through a depending end of the basket. A first catalyst slurry stream is removed from the basket 84 in the catalyst filter 81 in line 86 while a final heavy hydrocarbon rich coolant stream passes in line 88 to a coolant fractionation column 90.

With the bulk of the catalyst removed, the final heavy hydrocarbon rich coolant stream enters the coolant fractionation column 90. Since it is desired to obtain a coolant stream and a heavy product stream, the coolant fractionation column 90 is operated to separate two fractions, a heavy hydrocarbon purge stream rich in heavy hydrocarbon products comprising, in an embodiment, C4+ hydrocarbons in an overhead line 92 and a heavy hydrocarbon lean coolant stream in a bottoms line 94. The heavy hydrocarbon purge stream is withdrawn from an overhead of the coolant column 90 in the overhead line 92, condensed in a cooler and fed to a separator. A portion of the condensed heavy hydrocarbon purge stream is recycled to the coolant fractionation column 90 as reflux through a reflux line and the remaining portion of the condensed heavy hydrocarbon purge stream is withdrawn through a net heavy hydrocarbon purge stream in a net overhead line 93. The heavy hydrocarbon purge stream in line 93 may be transported and fed to the regenerator 20 in line 22 to serve as fuel to boost heat generation therein.

The heavy hydrocarbon lean coolant stream is withdrawn from the coolant column 90 through a bottoms line 94 from which a portion of the bottoms flows through a reboiler line and a reboiler heater and returns heated to the coolant column 90. The remaining portion of the heavy hydrocarbon lean coolant stream lean also of catalyst flows through bottoms line 95 to line 46 to be recycled as coolant to the contact cooler 34 via line 41 after mixing with the make-up coolant stream and the first cooled pump-around coolant stream in line 44.

The coolant column may operate at an overhead pressure of about 25 to about 50 kPa (gauge) and a bottoms temperature of about 200° C. to about 240° C.

The first catalyst rich, heavy hydrocarbon rich liquid coolant stream back in line 62 has a heavier loading of catalyst than the second catalyst rich, heavy hydrocarbon rich liquid coolant stream in line 76 because it is contacted with a reactor effluent stream with a heavier concentration of catalyst. Catalyst must be removed from the first catalyst rich, heavy hydrocarbon rich liquid coolant stream in line 62, so it is fed to a catalyst separation vessel 60.

The catalyst separation vessel 60 may comprise an outer shell and a plurality of cyclonic separators 100. The first catalyst rich, heavy hydrocarbon rich liquid coolant stream in line 62 may be fed to cyclone inlets disposed in the cyclones 100 in an inlet chamber 102 between two tube sheets. The cyclones 100 swirl the incoming catalyst rich coolant to centripetally separate heavier solid catalyst particles from lighter liquid coolant. A catalyst lean liquid coolant stream exits the cyclones above the inlet chamber 102 through a line 104, and a catalyst return stream comprising a catalyst slurry exits the cyclones below the inlet chamber 102 through a line 106. Catalyst separation vessel 60 may alternatively be a filter or other similar equipment for separating the first catalyst rich, heavy hydrocarbon rich liquid coolant stream in line 62 into the catalyst lean liquid coolant stream and the catalyst return stream.

The catalyst lean liquid coolant stream in line 104 may be further filtered in a filter 108 as described for filter 80 hereinabove to provide a more catalyst lean liquid coolant stream in line 110 and a second catalyst slurry stream in line 112. The more catalyst lean liquid coolant stream may be cooled and returned to the contact cooler after mixing with the heavy hydrocarbon lean coolant stream in the bottoms line 95, make up coolant stream in line 48 to generate the first recycled coolant stream in line 46. The first recycled coolant stream in line 46 mixes with the first cooled pump around coolant stream in line 44 to generate the first coolant stream in line 41 that is fed to the contact cooler 34 via the first coolant distributor 40.

The second catalyst slurry stream in line 112 may joined with the return catalyst stream in line 106. The return catalyst stream in line 106 supplemented with the second catalyst slurry stream in line 112 may be further supplemented with the first catalyst slurry stream in line 86 and transported back to the reactor 12 in line 116.

The return catalyst stream may be returned to the reactor 12 in at least one of two ways. In one way, the return catalyst stream is delivered directly to the reactor 12. In an aspect, the return catalyst stream may be used as a quench medium in line 32 that is contacted with the hot vaporous reactor effluent stream in the reactor 12 in which the fluid catalytic reaction occurs. In this way, the control valve on line 32 is opened. When delivered to the gas recovery conduit 28, the hydrocarbon will flash off the catalyst slurry in the return catalyst stream and be recovered with the gaseous products discharged from the reactor 12 through the reactor outlet 29 in line 30. The dried catalyst from the slurry will be separated from the gaseous products in the cyclones 27 and be returned to the catalyst bed, some of which returning to the reactor riser 14 to be contacted with feed. The other remaining catalyst from the bed will return to the regenerator 20 for regeneration and be returned to the reactor 12 after regeneration. It is also envisioned that line 32 can deliver the return catalyst stream to other parts of the reactor 12.

In another way, the return catalyst stream in line 116 is fed to the catalyst regenerator 20 before it is fed to the reactor 12. A line 118 may feed the return catalyst stream through an open control valve thereon to the catalyst regenerator 20. A line 120 with an open control valve thereon preferably transports the return catalyst stream from line 118 to a lower bed of catalyst in the catalyst regenerator 20. Alternatively, a line 122 with an open control valve thereon transports the return catalyst stream from line 118 to an upper collection bed of catalyst in the catalyst regenerator. However, other inlets to the catalyst regenerator 20 may receive the return catalyst stream. The hydrocarbon in the slurry may combust in the hot regenerator leaving regenerated catalyst that may be returned to the reaction step in the reactor 12 through the conduit 16.

The disclosed process provides a way to cool reactor effluent from a fluidized catalytic reactor while simultaneously recovering catalyst in the reactor effluent for recycle and recovering heavy hydrocarbon byproducts in the reactor effluent.

Specific Embodiments

While the following is described in conjunction with specific embodiments, it will be understood that this description is intended to illustrate and not limit the scope of the preceding description and the appended claims.

A first embodiment of the invention is a process for recovering catalyst from a fluidized catalytic reactor effluent comprising reacting a reactant stream by contact with a stream of fluidized catalyst to provide a vaporous reactor effluent stream comprising catalyst and products; contacting the vaporous reactor effluent stream with a liquid coolant stream; cooling the vaporous reactor effluent stream; transferring the catalyst into the liquid coolant stream; separating a catalyst lean vaporous reactor effluent stream from a catalyst rich liquid coolant stream; separating a return catalyst stream from the catalyst rich liquid coolant stream to provide a catalyst lean liquid coolant stream; and transporting the return catalyst stream back to the reacting step. An embodiment of the invention is one, any or all of prior embodiments in this paragraph up through the first embodiment in this paragraph wherein the vaporous reactor effluent stream comprises light hydrocarbon products and heavy hydrocarbon products and the liquid coolant stream is a solvent and further comprising absorbing the heavy hydrocarbon products into the liquid coolant stream to provide a catalyst lean, heavy hydrocarbon lean reactor effluent stream and a catalyst rich, heavy hydrocarbon rich liquid coolant stream. An embodiment of the invention is one, any or all of prior embodiments in this paragraph up through the first embodiment in this paragraph further comprising separating a heavy hydrocarbon purge stream from the heavy hydrocarbon rich liquid coolant stream to provide a heavy hydrocarbon lean liquid coolant stream. An embodiment of the invention is one, any or all of prior embodiments in this paragraph up through the first embodiment in this paragraph further comprising recycling the heavy hydrocarbon lean liquid coolant stream to the contacting step. An embodiment of the invention is one, any or all of prior embodiments in this paragraph up through the first embodiment in this paragraph further comprising filtering catalyst from the heavy hydrocarbon rich liquid coolant stream. An embodiment of the invention is one, any or all of prior embodiments in this paragraph up through the first embodiment in this paragraph further comprising recycling the catalyst lean liquid coolant stream back to the contacting step. An embodiment of the invention is one, any or all of prior embodiments in this paragraph up through the first embodiment in this paragraph further comprising filtering catalyst from the catalyst lean liquid coolant stream before recycling the catalyst lean liquid coolant stream to the contacting step. An embodiment of the invention is one, any or all of prior embodiments in this paragraph up through the first embodiment in this paragraph wherein the catalyst rich coolant stream is taken from a contact cooler at an intermediate location in the contact cooler. An embodiment of the invention is one, any or all of prior embodiments in this paragraph up through the first embodiment in this paragraph further comprising contacting the catalyst return stream with a hot vaporous reactor effluent stream in a reactor in which the reacting step occurs. An embodiment of the invention is one, any or all of prior embodiments in this paragraph up through the first embodiment in this paragraph further comprising separating a spent catalyst stream from the vaporous reactor effluent stream and passing the spent catalyst stream to a regenerator and transporting the catalyst return stream to the regenerator before transporting the catalyst return stream to the reacting step.

A second embodiment of the invention is a process for recovering catalyst from a fluidized catalytic reactor effluent comprising reacting a reactant stream over a stream of fluidized catalyst to provide a vaporous reactor effluent stream comprising catalyst and products including light hydrocarbons and heavy hydrocarbons; contacting the vaporous reactor effluent stream with a liquid coolant stream; cooling the vaporous reactor effluent stream; transferring the catalyst and absorbing the heavy hydrocarbon products into the liquid coolant stream to provide a catalyst rich, heavy hydrocarbon rich liquid coolant stream; separating a catalyst lean, light hydrocarbon rich vaporous reactor effluent stream from the catalyst rich, heavy hydrocarbon rich liquid coolant stream. An embodiment of the invention is one, any or all of prior embodiments in this paragraph up through the second embodiment in this paragraph further comprising separating a heavy hydrocarbon purge stream from the heavy hydrocarbon rich liquid coolant stream to provide a heavy hydrocarbon lean liquid coolant stream. An embodiment of the invention is one, any or all of prior embodiments in this paragraph up through the second embodiment in this paragraph further comprising recycling the heavy hydrocarbon lean liquid coolant stream to one of the contacting steps. An embodiment of the invention is one, any or all of prior embodiments in this paragraph up through the second embodiment in this paragraph further comprising filtering catalyst from the catalyst rich, heavy hydrocarbon rich liquid coolant stream. An embodiment of the invention is one, any or all of prior embodiments in this paragraph up through the second embodiment in this paragraph further comprising recycling the catalyst lean liquid coolant stream back to one of the contacting steps. An embodiment of the invention is one, any or all of prior embodiments in this paragraph up through the second embodiment in this paragraph further comprising filtering catalyst from the catalyst lean liquid coolant stream before recycling the catalyst lean liquid coolant stream to one of the contacting steps. An embodiment of the invention is one, any or all of prior embodiments in this paragraph up through the second embodiment in this paragraph further comprising separating a return catalyst stream from the catalyst rich liquid coolant stream to provide a catalyst lean liquid coolant stream, and transporting the return catalyst stream back to the reacting step.

A third embodiment of the invention is a process for recovering catalyst from a fluidized catalytic reactor effluent stream comprising reacting a reactant stream over a fluidized catalyst stream to provide a reactor effluent stream comprising catalyst and products; separating the vaporous reactor effluent stream from a spent catalyst stream; contacting the vaporous reactor effluent stream with a liquid stream; transferring the catalyst into the liquid stream to provide a catalyst rich liquid stream; separating a catalyst lean vaporous reactor effluent stream from the catalyst rich liquid stream; separating a return catalyst stream from the catalyst rich liquid coolant stream to provide a catalyst lean liquid coolant stream; and contacting the return catalyst stream with the vaporous reactor effluent stream. An embodiment of the invention is one, any or all of prior embodiments in this paragraph up through the third embodiment in this paragraph further comprising absorbing heavy hydrocarbon products into the liquid coolant stream to provide a heavy hydrocarbon rich liquid coolant stream. An embodiment of the invention is one, any or all of prior embodiments in this paragraph up through the third embodiment in this paragraph further comprising separating a heavy hydrocarbon purge stream from the heavy hydrocarbon rich liquid coolant stream to provide a heavy hydrocarbon stream.

Without further elaboration, it is believed that using the preceding description that one skilled in the art can utilize the present disclosure to its fullest extent and easily ascertain the essential characteristics of this disclosure, without departing from the spirit and scope thereof, to make various changes and modifications of the disclosure and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for recovering catalyst from a fluidized catalytic reactor effluent comprising:
reacting a reactant stream by contact with a stream of fluidized catalyst to provide a vaporous reactor effluent stream comprising catalyst and products;
contacting said vaporous reactor effluent stream with a liquid coolant stream in a contact cooler, wherein said vaporous reactor effluent stream is passed to a top of said contact cooler;
cooling said vaporous reactor effluent stream;
transferring said catalyst into said liquid coolant stream;
separating a catalyst lean vaporous reactor effluent stream from a catalyst rich liquid coolant stream;
separating a return catalyst stream from said catalyst rich liquid coolant stream to provide a catalyst lean liquid coolant stream; and
transporting said return catalyst stream back to said reacting step.

2. The process of claim 1 wherein said vaporous reactor effluent stream comprises light hydrocarbon products and heavy hydrocarbon products and said liquid coolant stream is a solvent and further comprising:
absorbing said heavy hydrocarbon products into said liquid coolant stream to provide a catalyst lean, heavy hydrocarbon lean reactor effluent stream and a catalyst rich, heavy hydrocarbon rich liquid coolant stream.

3. The process of claim 2 further comprising separating a heavy hydrocarbon purge stream from said heavy hydrocarbon rich liquid coolant stream to provide a heavy hydrocarbon lean liquid coolant stream.

4. The process of claim 3 further comprising recycling said heavy hydrocarbon lean liquid coolant stream to said contacting step.

5. The process of claim 3 further comprising filtering catalyst from said heavy hydrocarbon rich liquid coolant stream.

6. The process of claim 5 further comprising filtering catalyst from said catalyst lean liquid coolant stream before recycling said catalyst lean liquid coolant stream to said contacting step.

7. The process of claim 1 further comprising recycling said catalyst lean liquid coolant stream back to said contacting step.

8. The process of claim 7 wherein said catalyst rich coolant stream is taken from a contact cooler at an intermediate location in the contact cooler between a top and a bottom of said contact cooler.

9. The process of claim 1 further comprising contacting said catalyst return stream with a hot vaporous reactor effluent stream in a reactor in which said reacting step occurs.

10. The process of claim 1 further comprising separating a spent catalyst stream from said vaporous reactor effluent stream and passing said spent catalyst stream to a regenerator and transporting said catalyst return stream to said regenerator before transporting said catalyst return stream to said reacting step.

11. A process for recovering catalyst from a fluidized catalytic reactor effluent comprising:
reacting a reactant stream over a stream of fluidized catalyst to provide a vaporous reactor effluent stream comprising catalyst and products including light hydrocarbons and heavy hydrocarbons;
contacting said vaporous reactor effluent stream with a liquid coolant stream in a contact cooler, wherein said vaporous reactor effluent stream is passed to a location above a packing in said contact cooler;
cooling said vaporous reactor effluent stream;
transferring said catalyst and absorbing said heavy hydrocarbon products into said liquid coolant stream to provide a catalyst rich, heavy hydrocarbon rich liquid coolant stream;
separating a catalyst lean, light hydrocarbon rich vaporous reactor effluent stream from said catalyst rich, heavy hydrocarbon rich liquid coolant stream.

12. The process of claim 11 further comprising separating a heavy hydrocarbon purge stream from said heavy hydrocarbon rich liquid coolant stream to provide a heavy hydrocarbon lean liquid coolant stream.

13. The process of claim 12 further comprising recycling said heavy hydrocarbon lean liquid coolant stream to one of said contacting steps.

14. The process of claim 12 further comprising filtering catalyst from said catalyst rich, heavy hydrocarbon rich liquid coolant stream.

15. The process of claim 11 further comprising recycling said catalyst lean liquid coolant stream back to one of said contacting steps.

16. The process of claim 15 further comprising filtering catalyst from said catalyst lean liquid coolant stream before recycling said catalyst lean liquid coolant stream to one of said contacting steps.

17. The process of claim 11 further comprising: separating a return catalyst stream from said catalyst rich liquid coolant stream to provide a catalyst lean liquid coolant stream, and transporting said return catalyst stream back to said reacting step.

18. A process for recovering catalyst from a fluidized catalytic reactor effluent stream comprising:
reacting a reactant stream over a fluidized catalyst stream to provide a vaporous reactor effluent stream comprising catalyst and products;
separating said vaporous reactor effluent stream from a spent catalyst stream;
contacting said vaporous reactor effluent stream with a liquid stream;
transferring said catalyst into said liquid stream to provide a catalyst rich liquid stream;
separating a catalyst lean vaporous reactor effluent stream from said catalyst rich liquid stream;
separating a return catalyst stream from said catalyst rich liquid coolant stream to provide a catalyst lean liquid coolant stream; and
contacting said return catalyst stream with said vaporous reactor effluent stream.

19. The process of claim 18 further comprising absorbing heavy hydrocarbon products into said liquid coolant stream to provide a heavy hydrocarbon rich liquid coolant stream.

20. The process of claim 19 further comprising separating a heavy hydrocarbon purge stream from said heavy hydrocarbon rich liquid coolant stream to provide a heavy hydrocarbon stream.

* * * * *